United States Patent
Wang et al.

(10) Patent No.: US 7,476,766 B2
(45) Date of Patent: Jan. 13, 2009

(54) BIS(3-ALKOXYPROPAN-2-OL) SULFIDES, SULFOXIDES, AND SULFONES: NEW PREPARATIVE METHODS

(75) Inventors: Andrew Wilson Wang, Macungie, PA (US); Kevin Rodney Lassila, Macungie, PA (US); Michael Edward Ford, Trexlertown, PA (US); Joseph Richard Krock, Kunkletown, PA (US); Nancy Mary Martin, Allentown, PA (US); Ge Grace Zhang, Coopersburg, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 99 days.

(21) Appl. No.: 11/527,116

(22) Filed: Sep. 26, 2006

(65) Prior Publication Data
US 2007/0149821 A1 Jun. 28, 2007

Related U.S. Application Data

(62) Division of application No. 11/008,914, filed on Dec. 10, 2004, now Pat. No. 7,230,138.

(51) Int. Cl.
C07C 323/10 (2006.01)
C07C 319/00 (2006.01)
(52) U.S. Cl. .............. 568/32; 568/39; 568/62
(58) Field of Classification Search ............ 568/62, 568/32, 39
See application file for complete search history.

(56) References Cited
FOREIGN PATENT DOCUMENTS
DE 27 30 414 A1 7/1977
JP 09302029 11/1997

OTHER PUBLICATIONS

Rrosowsky, {Ethylene Oxides, In Heterocyclic Compounds, Weissberger, A. Ed.; John Wiley and Sons Inc.: New York, Part One, 1964, p. 327-330}.*

Brittain et al., Triphenylsilanethiol: A solid H2S equivalent in the ring opening of epoxides, Tetrahedron Letters, 34, (21), 1993, 3363-3366.*
Mahdavi et al. Synthesis of B-Dihydroxysulfides by Cleavage of Epoxides Using Quaternized Amino-Functionalized Cross-Linked Polyacrylamide as a New Polymeric Phase Transfer Catalyst. Phosphorus, Sulfur, and Silcon, 2005, vol. 180, pp. 1929-1936.*
U.S. Appl. No. 10/899,419, filed Jul. 26, 2004.

* cited by examiner

*Primary Examiner*—Sikarl A. Witherspoon
(74) *Attorney, Agent, or Firm*—Michael Leach

(57) ABSTRACT

Compounds according to formula (I)

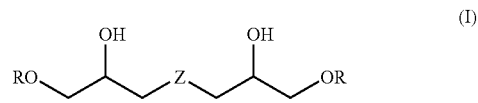

wherein Z is S, SO, or $SO_2$, may be prepared by a process that includes charging to a reactor hydrogen sulfide and an alkyl glycidyl ether according to formula (III), in the presence of a base.

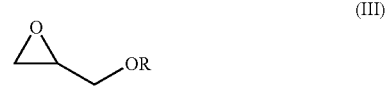

The compounds may also be prepared by contacting an alkoxychlorohydrin according to formula (II) with a sulfide source.

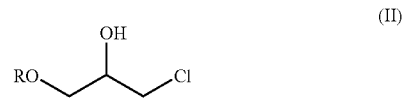

7 Claims, No Drawings

BIS(3-ALKOXYPROPAN-2-OL) SULFIDES, SULFOXIDES, AND SULFONES: NEW PREPARATIVE METHODS

CROSS-REFERENCE TO RELATED APPLICATIONS

This application is a divisional application and claims the benefit of priority under 35 USC 120 of U.S. application Ser. No. 11/008,914, filed 10 Dec. 2004 now U.S. Pat No. 7,230,138.

BACKGROUND OF THE INVENTION

This invention relates to surfactant compositions, and methods of making them. More particularly, it relates to preparation of bis(3-alkoxypropan-2-ol)sulfides, sulfoxides, and sulfones.

One particularly useful class of surfactants includes bis(3-alkoxypropan-2-ol)sulfides, sulfoxides, and sulfones. These compounds, depending upon their particular substituents, are capable of providing a wide range of equilibrium surface tension, dynamic surface tension, and foaming performance in a variety of applications. Therefore, methods of making such compounds efficiently are of considerable value. Copending U.S. patent application Ser. No. 10/899,419 discloses methods of making these materials by processes involving reaction of a sulfide source with a glycidyl ether to form the sulfide. In some cases, however, it may be desirable to prepare bis(3-alkoxypropan-2-ol)sulfides by methods in which more economical raw materials are used, and/or which provide greater control over the formation of undesirable side products.

BRIEF SUMMARY OF THE INVENTION

In one aspect, the invention provides a method of making a compound according to formula (I),

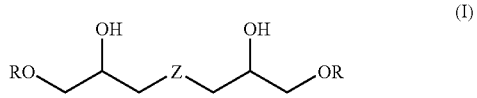

(I)

wherein each R is independently selected from the group consisting of C4-C20 branched, linear, and cyclic alkyl, alkenyl, aryl, and aralkyl moieties; C4-C20 branched, linear, and cyclic alkyl, alkenyl, aryl, and aralkyl moieties bearing a carbonyl group or one or more heteroatoms selected from O, S, and N; glycol ether moieties of the formula $R_3(OCH_2CH_2)_n$—; aminoethylene moieties of the formula $R_3(NHCH_2CH_2)_n$—; and thioether moieties of the formula $R_3S(CH_2)_n$—; wherein $R_3$ is H or linear C1-C12 alkyl and n is an integer from 1 to 15; and Z is S, SO, or $SO_2$. The method includes charging to a reactor a sulfide source and an alkoxychlorohydrin according to formula (II)

(II)

In another aspect, the invention provides a method of making a compound according to formula (I) as shown and defined above, including charging to a reactor water, a base, gaseous hydrogen sulfide, and a glycidyl ether according to formula (III)

(III)

DETAILED DESCRIPTION OF THE INVENTION

The present invention relates to novel methods of preparing bis(3-alkoxypropan-2-ol)sulfides, sulfoxides, and sulfones according to the following formula (I), wherein Z represents S, SO, or $SO_2$, respectively:

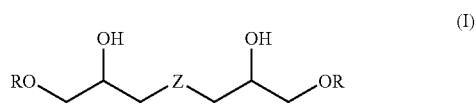

(I)

Each R is independently a C4-C20 alkyl, alkenyl, aryl, or aralkyl moiety, and may be branched, linear, or cyclic. It may also be such a moiety bearing a carbonyl group, especially a carboxylic acid, ester, or amide, and/or one or more heteroatoms selected from O, S, and N. Such moieties may be in any location on R. Typically R is a C8-C18 linear alkyl group, and more typically it is a C12-C16 linear alkyl group. R may also be a glycol ether moiety of the formula $R_3(OCH_2CH_2)_n$—, an aminoethylene moiety of the formula $R_3(NHCH_2CH_2)_n$—, or a thioether moiety of the formula $R_3S(CH_2)_n$—, wherein $R_3$ is H or linear C1-C12 alkyl and n is an integer from 1 to 15. Nonlimiting examples of suitable R groups include butyl, hexyl, octyl, 2-ethylhexyl, decyl, dodecyl, tetradecyl, hexadecyl, octadecyl, phenyl, cresyl (any isomer, attached at any ring position or at the phenolic oxygen), and mixtures thereof. Typically, the R groups will be one or more of butyl, 2-ethylhexyl, octyl, decyl, dodecyl, and tetradecyl.

Preparation of Compounds of Formula (I) from Alkoxychlorohydrins

In one aspect of the invention, compounds (I) wherein Z=S may be prepared by the reaction of a sulfide source with an alkoxychlorohydrin according to formula (II), wherein R is as defined above. Compounds wherein Z is SO or $SO_2$ may be made by oxidation of the corresponding compound where Z is S, using oxidation techniques well known in the art. In one exemplary embodiment of the invention oxidation is performed with hydrogen peroxide, for example as disclosed in copending U.S. patent application Ser. No. 10/899,419, but other methods may be used.

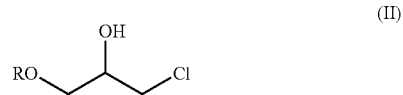

(II)

As used herein, the term "sulfide source" means a composition that contains, or otherwise provides, any of hydrogen sulfide, a bisulfide anion, or a sulfide anion. Suitable nonlimiting examples of sulfide sources include compounds selected from the group consisting of alkali metal sulfides, ammonium sulfide, alkali metal bisulfides, ammonium bisulfide, alkaline earth sulfides, and hydrogen sulfide. Specific examples of suitable sulfide sources include hydrogen sulfide, sodium sulfide, sodium bisulfide, potassium sulfide, potassium bisulfide, lithium sulfide, and lithium bisulfide in the anhydrous form or as hydrates. Other sulfide sources include alkali metal polysulfides and disulfides.

To prepare compounds according to formula (I), the sulfides or bisulfides may be reacted (adducted) in the presence of water and a base with the alkoxychlorohydrin, which may optionally be dispersed in a reaction medium including a diluent, at a temperature sufficiently high so as to provide a convenient reaction rate and sufficiently low so as to prevent significant by-product formation. By "dispersed," it is meant that the alkoxychlorohydrin is suspended in the medium, dissolved in it, or a combination of these.

For cost reasons, sodium sulfide or sodium hydrogen sulfide are typical sulfide sources, and can be used either as hydrates or as aqueous solutions. In practice, it is also generally desirable to use a phase transfer catalyst to enhance the transport of ions across the liquid-liquid phase boundary that commonly results due to insolubility of at least some of the organic components in the aqueous phase, which contains the base. In the absence of a phase transfer catalyst, ring-closing of the alkoxychlorohydrin (forming glycidyl ether) may predominate for some systems under some circumstances, with the subsequent reaction of glycidyl ether with sulfide being slower. More significantly, larger amounts of undesired by-products may be formed if a phase-transfer catalyst is not used. Any phase transfer catalyst may be used, with typical examples being quaternary ammonium halides, typically tetraalkylammonium chlorides or bromides.

The amount of alkoxychlorohydrin used in the reaction is typically from about 2.0 to about 5 moles per mole of sulfide, more typically from about 2 to about 3 moles, still more typically from about 2 to about 2.5 moles, and most typically about 2 moles per mole of sulfide. Mixtures of alkoxychlorohydrins may be employed such that the reaction mixture will contain alkoxychlorohydrins having two or more different R groups. In such a situation, the product may include a mixture of compounds according to formula (I) in which some have the same R groups on both sides of the molecule, while others have different embodiments of these groups on one side vs. the other. The reaction temperature may be in the range from about 50° C. to about 150° C., preferably from about 50° C. to about 130° C., and more preferably from about 60° C. to about 90° C. The optimum conditions will depend upon the specific reactants, the reactor configuration, the solvents employed, and other variables. A variety of diluents may be used for the reaction, including liquids in which one or more of the reactants is essentially insoluble. More typically, a diluent (if used) will be a material that is a solvent for one or more of the reactants. Examples of suitable solvents include, but are not limited to, isopropanol, ethanol, methanol, acetonitrile, ethylene glycol, propylene glycol, combinations of water and acetonitrile, combinations of water and methanol, combinations of water and isopropanol, combinations of water and ethanol, and mixtures thereof. Typically, the diluent will comprises excess alcohol ROH remaining from the production of the alkoxychlorohydrin, optionally in combination with water used to provide an aqueous phase, to keep the sulfide source and by-product salt in solution.

After the reaction of the sulfide source with the alkoxychlorohydrin is complete, byproduct salts such as NaCl may if desired be washed out of the product along with the phase-transfer catalyst, any residual base, and the Lewis acid catalyst (if present from preparation of the alkoxychlorohydrin; see below). This washing may for example be accomplished through a series of stages in which water is added to the reactor, the mixture is agitated for a period sufficient to contact the aqueous and organic phases thoroughly, and then allowed to phase-separate (settle). The aqueous layer is then drained off. This set of operations is typically repeated 2-5 times until the desired removal of these impurities is accomplished. Use of a very mildly acidic wash medium (such as very dilute acetic acid or dilute aqueous monosodium phosphate) may be preferred over pure water for one or more of the washes, in order to produce a nearly neutral final pH.

After washing, light impurities—chiefly residual water and any excess alcohol that may be present from the preparation of the alkoxychlorohydrin (see below)—are removed from the product, typically by stripping. Depending on the desired final product purity, this may be accomplished either by flashing off these materials under vacuum, with nitrogen sparge, at elevated temperatures. If a higher purity is required, a wiped-film evaporator or similar apparatus may be needed to accomplish the desired level of alcohol removal. Also, this alcohol removal can be done earlier in the process, such as after the alkoxychlorohydrin has been made but before the sulfide source is introduced.

In some exemplary embodiments of the invention, the sulfide source is hydrogen sulfide, whose use may provide advantages in terms of ease of manufacture and product purity. The use of gaseous hydrogen sulfide to charge the reactor makes it easier to provide a stoichiometric amount relative to the alkoxychlorohydrin. If too much hydrogen sulfide is allowed to react with the alkoxychlorohydrin, considerable amounts of the 1:1 alkoxychlorohydrin:sulfide adduct may be formed. However, since the reaction requires one mole of base per mole of alkoxychlorohydrin, one way to control the stoichiometry is to pressurize the reactor with hydrogen sulfide, then charge one-half mole of base per mole of alkoxychlorohydrin. Once this reaction is completed, the headspace of the reactor can then be purged of hydrogen sulfide (with nitrogen, for example). Then the remaining half mole equivalent of base can be added, and the reaction allowed to proceed to completion. Although it may generally be desirable to provide 0.5 mole of base in each

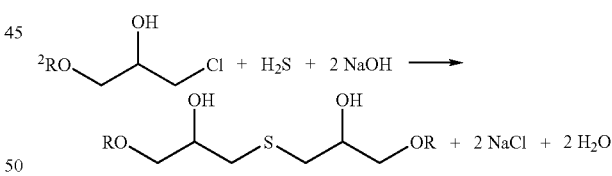

of the two portions, other amounts can be used without limit. Typically, however, the first portion of base will provide between about 0.1 and 0.9 mole equivalents of base, more typically between about 0.4 and 0.6 mole equivalents, in order to maximize formation of the desired 2:1 adduct.

An alternative way of controlling the reaction is simply to introduce one half mole of hydrogen sulfide for every mole of alkoxychlorohydrin charged to the reactor. Then one (or more) mole equivalent of base (relative to alkoxychlorohydrin) may be added, and the reaction allowed to proceed to completion. Although this example describes the use of one half mole of hydrogen sulfide for every mole of alkoxychlorohydrin, other amounts may be used. Typically, however, the amount will be between about 0.45 and 0.55 mole equivalents.

Preparation of Alkoxychlorohydrins

Alkoxychlorohydrins according to formula (II) may be made by any process known in the chemical art. In one embodiment of the invention, they may be prepared by reaction between an alcohol and epichlorohydrin, optionally in the presence of a Lewis acid (such as boron trifluoride, zinc chloride, titanium (IV) isopropoxide or stannous chloride) as a catalyst. Reaction occurs according to the following equation, where R is as defined above.

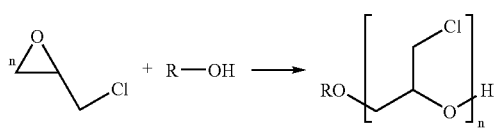

It is typically desired that products with n=1 be produced, with minimal formation of side products having higher n values. The selectivity of this reaction depends, inter alia, upon the amount of alcohol relative to epichlorohydrin. For a given set of conditions, the use of larger amounts of alcohol tends to provide higher proportions of the desired n=1 product. Because sulfide ion can potentially react with chlorine atoms in any of the alkoxychlorohydrin species (regardless of the value of n), the presence of significant amounts of n>1 molecules can lead to the formation of highly branched or oligomeric compounds in the final product mixture, which may impact product performance, toxicity and biodegradability. If the presence of chloride-containing, branched or oligomeric impurities does not matter in the market served by the product, however, an excess of alcohol may not be necessary. Therefore, the alcohol to epichlorohydrin molar ratio is typically between 0.8:1 and 4:1, more typically between 1.0:1 and 4:1, and most typically between 1.0:1 and 2:1. Typically, the epichlorohydrin is gradually added to the alcohol under time and temperature conditions that favor rapid reaction and correspondingly low concentration of epichlorohydrin in the reaction mixture. The reaction may be run under a variety of temperatures and pressures, with 60-100° C. and atmospheric pressure being typical and generally preferred. Rate of epichlorohydrin addition is limited both by the heat removal capacity of the equipment and the rate of consumption of epichlorohydrin. For safety and selectivity reasons it is preferable not to accumulate epichlorohydrin in the reactor. Once addition of epichlorohydrin is complete, the reactor contents are held at temperature for a period of time sufficient to ensure complete conversion of the epichlorohydrin to alkoxychlorohydrin.

Preparation of Compounds of Formula (I) from Glycidyl Ethers

In another aspect of the invention, compounds (I) wherein Z=S may be prepared by the reaction of hydrogen sulfide with a glycidyl ether according to formula (III), wherein R is as defined above. As noted above, compounds wherein Z is SO or SO$_2$ may be made by oxidation of the corresponding compound where Z is S, using oxidation techniques well known in the art.

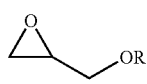

(III)

Hydrogen sulfide is supplied in gaseous form to a reactor under basic aqueous conditions, where the hydrogen sulfide or a salt thereof reacts with two moles of the glycidyl ether to form the desired product. The reactor is preferably initially charged with a diluent in which the hydrogen sulfide is soluble, for example an aqueous solution of a base such as sodium hydroxide. The glycidyl ether may then be added gradually to the reactor to control the rate and stoichiometry of reaction. The amount of glycidyl ether charged to the reactor is typically from about 2.0 to about 5 moles per mole of hydrogen sulfide, more typically from about 2 to about 3 moles, still more typically from about 2 to about 2.5 moles, and most typically about 2 moles per mole of sulfide. Mixtures of glycidyl ethers may be employed such that the reaction mixture will contain glycidyl ethers having two or more different R groups. In such a situation, the product may include a mixture of compounds according to formula (I) in which some have the same R groups on both sides of the molecule, while others have different embodiments of these groups on one side vs. the other.

The reactants are dispersed in a reaction medium including a diluent, and the reaction is run at a temperature sufficiently high so as to provide a convenient reaction rate and sufficiently low so as to prevent significant by-product formation. By "dispersed," it is meant that as it is added, the glycidyl ether is suspended in the medium, dissolved in it, or a combination of these. The reaction temperature may be in the range from about 50° C. to about 150° C., preferably from about 50° C. to about 130° C., and more preferably from about 60° C. to about 90° C. The optimum conditions will depend upon the specific reactants, the reactor configuration, the diluent(s) employed, and other variables. A variety of diluents may be used for the reaction, including liquids in which one or more of the reactants is essentially insoluble. More typically, the diluent (if used) will be a material that is a solvent for one or more of the reactants. Examples of suitable solvents include, but are not limited to, water, isopropanol, ethanol, methanol, acetonitrile, ethylene glycol, propylene glycol, combinations of water and acetonitrile, combinations of water and methanol, combinations of water and isopropanol, combinations of water and ethanol, and mixtures thereof. Typically, water will be used. After the reaction is complete, the product may be isolated using washing, stripping, and other workup procedures known to those of ordinary skill in the chemical art.

In one exemplary embodiment, reaction of the sulfide source with the glycidyl ether may be performed as follows. Water containing a small amount of base (for example, sodium hydroxide) and an optional phase-transfer catalyst is charged to the reactor. The base serves a catalytic function, and therefore no specific amount is required. Typically, the amount of base will equal between 0.001 and 0.1 mole equivalents, more typically between 0.001 and 0.025 mole equivalents, relative to the total charge of glycidyl ether. The reactor is then purged with nitrogen or other inert gas and then pressurized with gaseous hydrogen sulfide. A pressure of 25-250 psig is typical, but any pressure may be used. Agitation is provided to ensure acceptable gas-liquid contact, and a portion (typically half) of the total amount of glycidyl ether is then gradually added to the reactor. The rate of addition may be limited by the heat removal capability of the reactor, but in any case it may be desirable to use a rate slow enough that large concentrations of glycidyl ether do not accumulate in the reactor, for reasons of both safety and product purity. Once half of the glycidyl ether has been charged and allowed to react, the reactor headspace is thoroughly purged of hydrogen sulfide with nitrogen or another inert gas. Then the remaining glycidyl ether is gradually added and allowed to react. This sequence of steps helps to increase the yield of the desired 2:1 glycidyl ether:sulfide adduct. The example given here describes a 2-step addition of the glycidyl ether, in equal portions. The portions need not be equal, however, and the molar ratio of the first to the second portion may range between 0.7:1 and 1.3:1, typically between 0.9:1 and 1.1:1, and most typically between 0.95:1 and 1.05:1. Post-reaction operations usually include washing away residual base and phase transfer catalyst and stripping to remove water from the product, as described above.

Preparation of Glycidyl Ethers

Glycidyl ethers for use in preparing bis(3-alkoxypropan-2-ol)sulfides according to the foregoing method may be prepared from alkoxychlorohydrins, whose preparation has been outlined above. One exemplary method involves treatment of an alkoxychlorohydrin with base, resulting in ring closure to form the glycidyl ether. Methods for such conversions are widely known to the person of ordinary skill in the art. However, any source of glycidyl ether may be used.

EXAMPLES

Example 1

Production of Dodecyloxychlorohydrin from Epichlorohydrin

1-Dodecanol (279.5 grams) was charged to a one-liter, oil-jacketed glass reactor equipped with a direct-drive stirrer and overhead condenser. The vessel was continuously purged with nitrogen and heated to 75° C. Stannic chloride (2.26 grams) was added, then epichlorohydrin was added at a rate of 1.5 mL/min to a total of 58.66 mL (69.4 grams, corresponding to a 1:2 mole ratio of epichlorohydrin to 1-dodecanol). At the intermediate points corresponding to 1:3 and 1:4 epichlorohydrin to 1-dodecanol ratio, the feed of epichlorohydrin was interrupted and the solution was allowed to react for a few minutes, then sampled for analysis by gas chromatography. Similarly, the final solution was maintained for two hours at 80° C. prior to analysis. The results of these analyses are given in Table 1, below, where the integer n is defined as in the following equation and wherein the reported values are area % figures determined by gas chromatography.

TABLE 1

| $C_{12}H_{25}OH$/Epi Mole ratio | $C_{12}H_{25}OH$ | $C_{12}$ Chlorohydrin (n = 1) | $C_{12}$ Side Products (N > 1) |
|---|---|---|---|
| 4:1 | 70.64 | 25.40 | 0.22 |
| 3:1 | 62.40 | 32.88 | 0.49 |
| 2:1 | 46.19 | 47.82 | 1.27 |
| 1.35:1 | 26.22 | 62.68 | 2.62 |
| 1.27:1 | 21.06 | 67.46 | 3.84 |
| 1.17:1 | 14.34 | 72.22 | 5.45 |

Since the materials in Table 1 have a GC response factor roughly proportional to their molecular weight, these results indicate that using a 1-dodecanol to epichlorohydrin molar ratio of two or greater was capable of producing a product containing less than 3.0 weight percent of the undesirable (n>1) adducts, relative to the total weight of the mixture of all adducts (n=1 and n>1).

Example 2

Preparation of bis(3-alkoxypropan-2-ol)sulfides from Alkoxychlorohydrins

Mixed alkoxychlorohydrins were prepared by reacting 621.2 grams of a commercially available mixture of 1-decanol, 1-dodecanol, 1-tetradecanol and 1-hexadecanol (approximately 1, 66, 27 and 6 weight percent, respectively) with 149.1 grams of epichlorohydrin in the presence of stannic chloride (3.1 grams), as described in Example 1. The resulting mixture was heated to 80° C., and 124.2 grams of 50 weight percent aqueous sodium hydroxide was added. Next, tetrabutylammonium bromide (3.1 gram) was added. A 45 weight percent solution of NaSH in water was prepared, and 99.4 grams of this was added to the reactor. The reactor contents were stirred at 80-90° C. for five hours, then cooled overnight. Analysis by gas chromatography showed that conversion of the mixed alkoxychlorohydrins had leveled off at a greater than 95% consumption level. The next day, the contents were reheated to 75° C., then the stirring was stopped and the organic and aqueous phases were allowed to separate. The aqueous layer was then drained off. The reactor contents were washed four times with approximately 200 mL of water each time. Each wash step consisted of adding the water, agitating for 15 minutes, then stopping the agitation and allowing 30 minutes for the phases to separate prior to draining off the aqueous phase. Finally, the product was purified by removing the excess alcohols, alkoxychlorohydrins and water via short-path distillation at 150° C. and ~1 torr absolute pressure. The product identity was confirmed by LC/MS (liquid chromatography/mass spectrometry) and the purity was estimated to be >95%, with less than 1.5% of the starting alcohols remaining in the final product.

Example 3

Preparation of bis(3-butoxypropan-2-ol)sulfide from Butyl Glycidyl Ether

Distilled water (150 mL), 2-propanol (150 mL), tetrabutylammonium bromide (2.0 grams) and sodium hydroxide (0.8 grams) were charged to a 1000 mL Parr reactor. The reactor contents were heated under nitrogen to 60° C. with constant agitation. A 2250 mL ballast cylinder was pressurized with hydrogen sulfide to 248 psig and then isolated from the hydrogen sulfide supply. The reactor was then pressurized to 100 psig from the ballast. Next, butyl glycidyl ether was fed at 2 mL/min, to a total of 100 mL, with the ballast remaining open to the reactor and the reactor pressure set using a forward pressure regulator. After the 100 mL of butyl glycidyl ether was added, the reaction was allowed to continue until the uptake of hydrogen sulfide ceased. At that point the reactor was cooled to 30° C., and the reactor headspace was vented and purged several times with nitrogen to remove hydrogen sulfide. The reactor contents were again heated to 60° C., and another 100 mL of butyl glycidyl ether was then added at a rate of 5 mL/min. The reactor contents were maintained at 60° C. for roughly 7 hours, and then cooled. An analysis of the contents showed that a small amount of the 1:1 glycidyl ether:$H_2S$ adduct (BuO—$CH_2$—CH(OH)—$CH_2SH$) was still present, so the reactor was reheated to 60° C., 40 mL of butyl glycidyl ether was added, and the reactor contents were again maintained at 60° C. for 7 hours. Analysis of the final material showed essentially quantitative conversion of the butyl glycidyl ether to the desired 2:1 glycidyl ether:$H_2S$ adduct, with approximately 0.8 weight percent excess butyl glycidyl ether remaining in the product.

Example 4

Preparation of bis(3-dodecyloxypropan-2-ol)sulfide from Dodecyloxychlorohydrin

A 450-gram portion of 60 weight percent dodecyloxychlorohydrin (balance 1-dodecanol) was charged to a 1000 mL Parr reactor, along with 150 mL of distilled water and 2.0 grams of tetrabutylammonium bromide. The reactor was purged with nitrogen, and the contents were then heated under nitrogen to 75° C. with constant agitation. A 2250 mL ballast cylinder was pressurized with hydrogen sulfide to 248 psig and then isolated from the hydrogen sulfide supply. The reactor was then pressurized to 100 psig from the ballast. NaOH (50% aqueous) was then fed to the reactor at a rate of 0.5 mL per minute, to a total of 24.2 mL (36.66 grams). The reaction was allowed to proceed to completion, then the hydrogen sulfide ballast was valved off from the reactor, the contents were cooled to room temperature, and the reactor headspace was purged and vented to remove all hydrogen sulfide. The reactor contents were then reheated to 75° C., and another 24.2 mL of 50% NaOH was added, again at 0.5 mL per minute. The reactor contents were maintained at 75° C. for two hours, then cooled to room temperature. Analysis of the reaction product by gas and liquid chromatography showed 70% conversion of the dodecyloxychlorohydrin with greater than 95% selectivity to the desired product.

Example 5

Preparation of bis(3-alkoxypropan-2-ol)sulfides from Alkoxychlorohydrins

A 621.2-gram portion of a mixed linear alcohol stream consisting of roughly 0.6 weight percent 1-decanol, 66.2 weight percent 1-dodecanol, 27.4 weight percent 1-tetradecanol and 5.8 weight percent 1-hexadecanol was converted to the corresponding alkoxychlorohydrin mixture using the process in Example 1. A 3.1-gram charge of tin (IV) chloride and 149.1 grams of epichlorohydrin were used in this reaction. Once the reaction was complete, 207 grams of distilled water and 3.1 grams of tetrabutylammonium bromide were added. When the temperature of the reactor contents had stabilized at 77° C., 99.5 grams of 45 weight percent aqueous sodium hydrogen sulfide solution were gradually added over a two-hour period. The reactor temperature was maintained in the 70-75° C. range throughout the addition period. The reactor contents were then maintained for four hours at 75-95° C. to ensure completeness of reaction.

With the reactor held at roughly 85° C., the aqueous (brine) layer (477.6 grams) was then drained off. The organic layer was then washed three times with 207 grams of distilled water per wash, allowing at least 30 minutes mixing time per wash and draining off the wash water each time. Bulk water was then removed from the product by vacuum stripping at 6 torr absolute pressure and 87° C. Removal of the Cl 0-Cl 6 alcohols was accomplished by short-path distillation at <1 torr absolute pressure and a jacket temperature of 160° C. The finished product contained less than 1.0 weight percent residual linear alcohols and was over 95% selective to the desired products.

Although the invention is illustrated and described herein with reference to specific embodiments, it is not intended that the subjoined claims be limited to the details shown. Rather, it is expected that various modifications may be made in these details by those skilled in the art, which modifications may still be within the spirit and scope of the claimed subject matter and it is intended that these claims be construed accordingly.

The invention claimed is:

1. A method of making a compound according to formula (I),

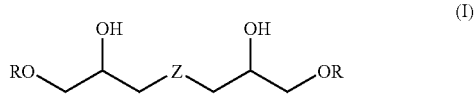

wherein each R is independently selected from the group consisting of C4-C20 branched, linear, and cyclic alkyl, alkenyl, aryl, and aralkyl moieties; C4-C20 branched, linear, and cyclic alkyl, alkenyl, aryl, and aralkyl moieties bearing a carbonyl group or one or more heteroatoms selected from O, S, and N; glycol ether moieties of the formula $R_3(OCH_2CH_2)_n$—; aminoethylene moieties of the formula $R_3(NHCH_2CH_2)_n$—; and thioether moieties of the formula $R_3S(CH_2)_n$—; wherein $R_3$ is H or linear C1-C12 alkyl and n is an integer from 1 to 15; and Z is S, SO, or $SO_2$;

the method comprising charging to a reactor water, a base, gaseous hydrogen sulfide, a glycidyl ether according to formula (III)

wherein R is as defined above, and a phase transfer catalyst which comprises a quaternary ammonium halide.

2. The method of claim 1, wherein a molar ratio of the base to the compound of formula (III) is between 0.001:1 and 0.1:1.

3. The method of claim 1, wherein a molar ratio of the base to the compound of formula (III) is between 0.001:1 and 0.025:1.

4. The method of claim 1, wherein the charging of the water, the base, the gaseous hydrogen sulfide, and the glycol ether comprises first charging the water, the base, and the gaseous hydrogen sulfide to form an aqueous phase, and then adding a first portion of the glycol ether to the reactor.

5. The method of claim 4, further comprising, after adding the first portion of glycidyl ether, removing gaseous hydrogen sulfide from the reactor and then adding a second portion of the glycidyl ether to the reactor.

6. The method of claim 5, wherein a molar ratio of the first portion of glycidyl ether to the second portion is between 0.7:1 and 1.3:1.

7. The method of claim 5, wherein a molar ratio of the first portion of glycidyl ether to the second portion is between 0.95:1 and 1.05:1.

* * * * *